(12) United States Patent
Veal, Jr.

(10) Patent No.: US 6,515,481 B2
(45) Date of Patent: Feb. 4, 2003

(54) STREAMING CURRENT DETECTOR WITH EASILY REMOVABLE MATCHED SLEEVE AND PISTON SET

(76) Inventor: Charles R. Veal, Jr., 4730 Coppedge Trail, Duluth, GA (US) 30096-2970

( * ) Notice: Subject to any disclaimer, the term of this patent is extended or adjusted under 35 U.S.C. 154(b) by 0 days.

(21) Appl. No.: 09/788,762

(22) Filed: Feb. 21, 2001

(65) Prior Publication Data
US 2002/0113597 A1 Aug. 22, 2002

(51) Int. Cl.⁷ .............................................. G01N 27/60
(52) U.S. Cl. .................... 324/453; 324/71.1; 73/863.83
(58) Field of Search ................................ 324/453, 71.1; 73/863.82, 863.83

(56) References Cited

U.S. PATENT DOCUMENTS

| | | | | |
|---|---|---|---|---|
| 4,446,435 A | * | 5/1984 | Canzoneri | 324/453 |
| 4,769,608 A | * | 9/1988 | Bryant | 324/453 |
| 5,119,029 A | * | 6/1992 | Bryant | 324/453 |

* cited by examiner

*Primary Examiner*—Christine Oda
(74) *Attorney, Agent, or Firm*—Harry I. Leon; Vivian L. Steadman

(57) ABSTRACT

A streaming current detector having a probe in which dielectric elements used to generate the streaming current—specifically, a sleeve for slideably receiving a reciprocating piston and the piston itself—can be replaced independently of the electrodes. Paired electrodes, each positioned proximate with one of the distal ends of the sleeve, are mounted on immobile structures other than the sleeve. The latter include a housing which forms a sheath for the sleeve and a retaining fitting. Threadedly engaged with the housing, this fitting also holds the sleeve in place. Generally, removal and replacement of each probe element can be accomplished in the field in under one minute. Costs of the dielectric elements are only a small fraction of those in the prior art, allowing a consumer to replace them much more frequently, as well as to substitute matched dielectric elements designed for their chemical and/or physical compatibility with a particular test fluid.

8 Claims, 4 Drawing Sheets

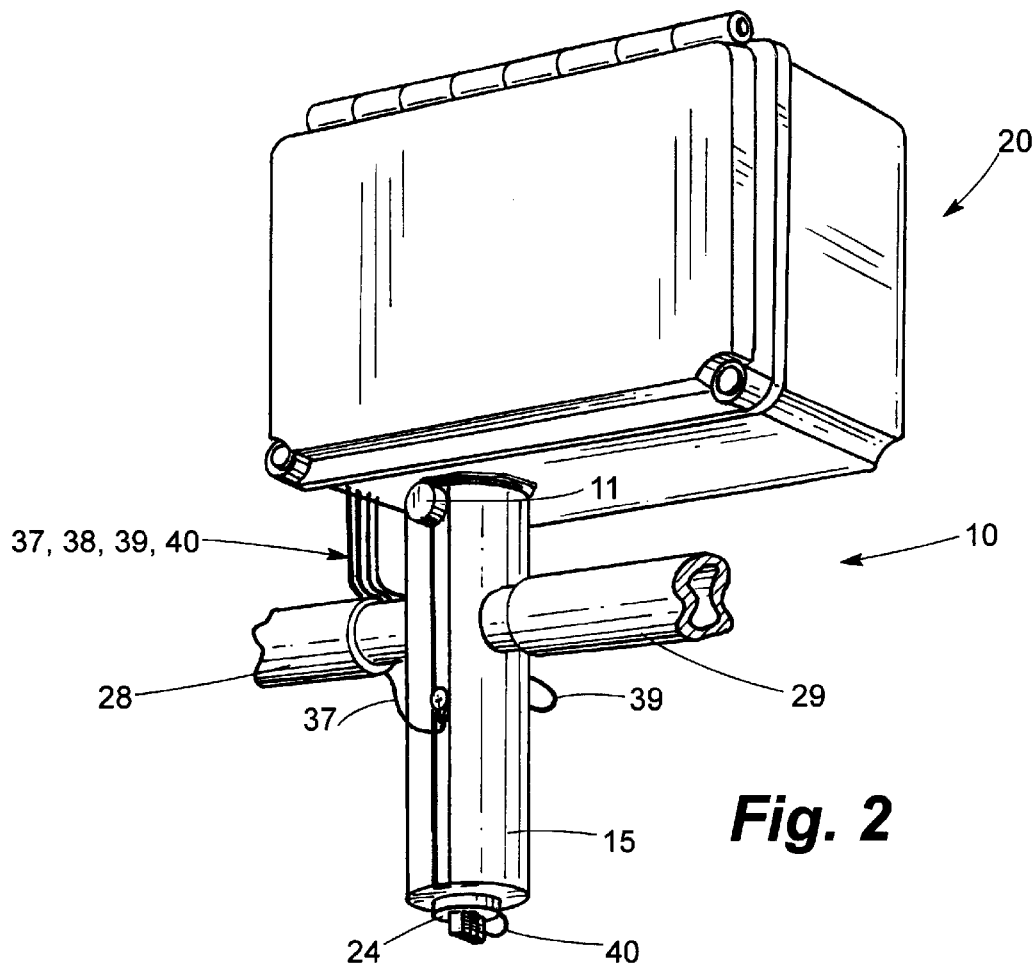
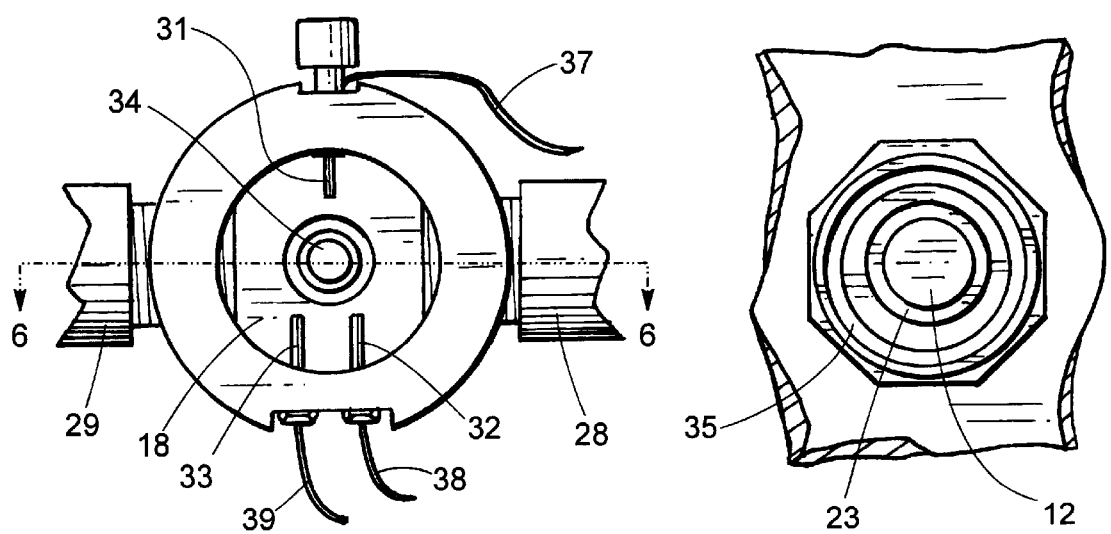

STREAMING CURRENT DETECTOR WITH EASILY REMOVABLE MATCHED SLEEVE AND PISTON SET

BACKGROUND OF THE INVENTION

Streaming current detectors take advantage of physical phenomena in which an ionic flux is produced by rapid movement between a pair of spaced apart, but close-fitting dielectric elements, the surfaces of which carry electrical charges induced by a charge-bearing fluid which bathes both elements. Ions or charged colloids adsorbed on the dielectric walls—which may include remnants of an earlier test fluid—give this ionic flux its unique characteristics. In a typical streaming current detector, the spaced apart dielectric elements are fabricated of Teflon R and include a piston and a bore for slideably receiving the piston; clearances between them measure about 0.005 inch.

To transmit a "streaming current", two electrodes, interconnected by an external circuit, are mounted proximate with the paired dielectric elements. A popular combination, taught by Bryant and Veal in U.S. Pat. No. 4,769,608, is to secure ring-like electrodes to the wall of the bore. An electrical signal is generated when the fluid attains a state of hydrodynamic shear as the close-fitting dielectric surfaces move past each other. The strength of this signal is dependent upon, among other things, the conductivity of the fluid, its velocity, the size of the fluid passageway, and the frequency of oscillation of the piston, as well as the presence of adsorbed species on the piston and bore surfaces.

While the usefulness of streaming current measurements for controlling the amount of chemicals needed to treat water, as well as various wastewater streams, is now widely recognized, operators trying to obtain such measurements, and have them be both continuous and reliable, still face daunting challenges. Not only does the buildup of contaminants on the electrodes or surfaces disposed proximate with them degrade the signal but also its strength can be reduced, with detrimental consequences, by numerous factors. Among them is an increase in the conductivity of the test fluid, a change which by itself can dramatically attenuate the streaming current signal. Indeed, if the conductivity goes high enough—to at least about 10,000 micromhos, the electrodes themselves short out. An operator could think, based on his streaming current observations, that he needs to add fewer chemicals or replace the dielectric elements and/or electrodes, when the real problem is that the process flow stream has experienced a sudden, unexpected increase in its electrolyte concentration.

Nor has a long-standing debate as to what the streaming current—sometimes referred to as the "streaming potential"—actually represents helped this situation. Getting beyond the basic assumption, i.e., the streaming current is related in some way to the surface charge or surface potential (zeta potential) of dispersed colloidal particles in a given system,.to an understanding of the zeta potential-streaming current detector response interrelationship remains an elusive goal. In view of this uncertainty, no one ventured to equip any of the prior art detectors with a compensating conductivity probe, even though the pronounced effects which changes in conductivity have on the streaming current are well known.

To circumvent conductivity-related distortions of the streaming current signal, prior art detectors have been relegated to a minor role in applications where the electrolyte concentration in a process flow stream varies widely. As part of an elaborate titration apparatus, the detector is used only to indicate when, as each discrete batch of test fluid is being titrated, the streaming current vanishes. The complexity of this apparatus introduces its own set of technical problems, as Krah discloses in U.S. Pat. No. 5,408,185.

On the other hand, progress towards eliminating streaming current aberrations caused by slow fouling is apparent in the prior art. Recognition came rather quickly that desorbing high molecular weight polymers once they are adsorbed on a Teflon R or similar dielectric material is virtually impossible in an on-line instrument. Instead, Bryant,and Veal invented an electrode holder which can be removed and replaced in less than one minute. As disclosed in U.S. Pat. No. 5,119,029, this holder included both the bore and the electrodes in a single unit. Problems with its use arose when operators seeking to rehabilitate holders soaked them in cleaning solution and inadvertently shorted out the electrical connections to the electrodes.

Attempts to provide reliable streaming current signals in situations where fouling occurs abruptly have been less successful. Problems with scaling in certain situations are so severe as to make the use of prior art detectors, including those equipped with removable electrode holders, cost prohibitive. In particular, lime scaling—which occurs wherever lime, a popular water treatment chemical, is used to coagulate/precipitate contaminants from a flow stream—has been inherently difficult to deal with.

Other conditions under which prior art remedies have proven inadequate involve the presence of grit or heavy silt in the test fluid. Not only do grit and heavy silt scratch less wear-resistant dielectric surfaces but also they introduce hairline crevasses along which charge-laden debris can accumulate. Jammed into the narrow fluid flow channels in a streaming current detector, grit can even cause a bore-mounted ring electrode to break or become dislodged. Pre-sample filters, strainers and hydrocyclone samplers have all been introduced to reduce grit, heavy silt and debris build-up within streaming current detectors but have failed to eliminate these troublesome impediments. dislodged. Pre-sample filters, strainers and hydrocyclone samplers have all been introduced to reduce grit, heavy silt and debris build-up within streaming current detectors but have failed to eliminate these troublesome impediments.

SUMMARY OF THE INVENTION

An object of the present invention is to provide a streaming current detector in which the replacement of critical parts used to generate the test signal, such as the dielectric elements and the electrodes, can be accomplished quickly, easily and independently of each other, so that the detector can be used in situations in which the corrosive and/or abrasive nature of the test fluid formerly made any use of a streaming current detector cost prohibitive.

A further object of the present invention is to provide such a detector in which the dielectric elements and the electrodes can be replaced in the field in less than one minute, virtually eliminating downtime.

A still further object of the present invention is to provide an improved streaming current detector having a matched set of removable dielectric elements, respective matched sets being designed in the basis of their capacity to withstand abrasive environments, as well as their chemical compatibility with the test fluid and the operating temperature of the process flow stream.

A still further object of the present invention is to provide such a detector in which the matched set of dielectric elements can be selected to increase the strength of the test signal over that generated by a conventional piston and bore combination, a tight-fitting pair being used in applications where extra response is needed. Alternately, a "loose-fitting" pair can be selected for those situations in which large particles are present or the sensitivity needs to be reduced.

The intent of the present invention is also to provide for electrodes that are less vulnerable to breakage during ruse and can be easily inspected and removed for cleaning, so that the remaining components of the detector can be soaked in solution without simultaneously shorting out electrode connections.

Another object of this invention is to monitor the conductivity and streaming current of a test fluid simultaneously, so that sources of test signal variations can be better understood, especially in common applications such as municipal wastewater treatment where wide swings in conductivity often occur as a result of road salting, an event which has delayed, largely unpredictable impacts as melting runoff enters a sewerage collection system.

Accordingly, there is provided a very stable: and reliable detector for the measurement of the streaming current in water or wastewater that can be operated over long periods of time, nearly continuously, without having to be shut down for either cleaning or repair/replacement of critical parts. The detector includes a probe with a housing, an elongated hollow sleeve for slideably receiving a reciprocating piston, and the piston itself. Sensing electrodes, which are positioned proximate with the distal ends of the sleeve, are mounted on immobile structures other than the sleeve. These structures include the housing and a retaining fitting.

Prior to use, the sleeve is slideably inserted into a cylindrical void formed in the housing and secured therewithin by the retaining fitting. A shoulder on the housing forms a stop which abuts the upper end of the sleeve when it is inserted as far as possible into the housing. The retaining fitting, in the preferred embodiment, is a closure plug threadedly engageable with internal threads formed within the lower end of the housing. In the assembled detector, as the retaining fitting is tightened on these threads, a gasket juxtaposed between it and the sleeve is compressed, forming a leak-tight seal between the fitting and the housing.

The housing further defines a transverse passageway fluidly connected to the sleeve. As the piston reciprocates, samples of a test flow stream directed through the transverse passageway, are alternately sucked into and expelled from a narrow, elongated flow channel of capillary width formed between the piston and the sleeve. The test flow stream flowing in the transverse passageway moves over the flow channel entrance with sufficient velocity to wash away any floc that might otherwise accumulate there.

Like the sleeve, that portion of the reciprocating piston which it slideably receives, i.e., the "active segment", can be easily replaced within the improved detector. Distal from the active segment, the piston is threadedly engaged with a guide, the only direct linkage between the piston and a mechanism for forcing it into repetitive upward and downward motions. Access to the piston above its active segment requires removal of the housing itself, a feat which, in the preferred embodiment, can be accomplished by disengaging a single pinch bolt or, alternately, a thumbscrew. This fastener is used to secure the housing to a downwardly protruding structural member through which the guide slides; and the structural member in turn is affixed to a protective casing for a synchronous motor and other components of the piston-driving mechanism.

In addition, each of the sensing electrodes is readily accessible and, like the sleeve and the reciprocating piston, can be removed independently of other probe elements. Generally, removal and replacement of each probe element can be accomplished in the field in less than one minute. No special tools are required.

In the preferred embodiment, the sensing electrode mounted on the closure plug can also be unscrewed with this plug, giving a user the option of simultaneously replacing both it and the sensing electrode or discarding only the electrode and installing a new one in its place.

Each electrode, whether it is mounted on the retaining fitting or the housing itself, can be threadedly advanced into the probe, so that the strength of the streaming current signal, diminished as electrode surfaces wear down, can be regained. Moreover, the electrodes in the improved detector are mounted so that they contact the test fluid just outside of the region where the close-fitting dielectric surfaces slide past each other. Thus, the rate at which the electrodes erode is reduced relative to what it would be if they were mounted inside these regions, as is the likelihood of the electrodes breaking or becoming dislodged.

Since the cost to make the dielectric sleeve is about 1/100th the cost of the removable electrode holder taught by Bryant and Veal in U.S. Pat. No. 5,119,029, consumers can afford to use the improved detector under conditions in which the corrosive and/or abrasive nature of the test fluid formerly made use of a streaming current detector cost prohibitive. The detector can even be used in situations in which there is severe lime scaling with this advance, a vast array of wastewater treatment processes can be controlled on-line, for the first time, using streaming current detectors.

Generally, the substantially lower cost of the sleeve makes more frequent replacement of both dielectric elements practicable. The more often they can be replaced, the more often the probe can be restored to its "original" condition, thereby obviating the test signal-degrading effects of fouling—whether due to scaling, chemical adsorption, or oil deposition—and of wear which alters the flow channel between the sleeve and-the active segment. Moreover, utilizing a new set of an otherwise identical sleeve and piston combination allows an operator to precisely calibrate the response of a system when a different chemical additive is introduced into a process flow stream; remnants of an earlier additive adsorbed on the dielectric elements can no longer distort the results.

In the preferred embodiment, the sleeve and piston are a matched set fabricated from materials and having clearances that are optimized for use with a particular test fluid. Preferably, sleeve/piston sets formulated of scratch-resistant ceramics are employed when abrasives are present in the sample flow stream and of glass when exposure to highly corrosive substances is likely. Moreover, as a rule, loose-fitting sleeve and piston combinations work best when grit and silt or other large particles are present in the test fluid.

Removable matched piston and sleeve sets also introduce a way for operators to adjust the strength of the streaming current signal mechanically. Heretofore, such adjustments were limited to manipulating electronic components. By using a "tight-fitting" matched set, one in which there is less clearance between the sleeve and the active segment, an extra strong signal response can be obtained. Alternately, the sensitivity of the detector can be reduced by utilizing a "loose-fitting" sleeve/piston pair.

Together with a first pair of sensing electrodes coupled to an electronic circuit which detects an alternating current flowing between them, the improved detector further comprises a second pair of sensing electrodes. The latter, which is preferably mounted on the housing in close proximity both to one of the first pair of electrodes and to the transverse passageway, is part of a conductivity probe integrated into the improved detector. A feed forward signal, proportional to a direct current flowing between the second pair of electrodes, is used to increase or decrease the amplifier gain for the streaming current raw signal in such a way that the latter is modified in direct proportion to changes in the direct current. The net result is that a conductivity-compensated streaming current is generated. Alternately, the conductivity can be measured independently of the streaming current.

BRIEF DESCRIPTION OF THE DRAWINGS

Further details are explained below with the help of the examples illustrated in the attached drawings in which:

FIG. 2 is a right side perspective view of the assembled detector according to FIG. 1;

FIG. 3 is a top plan view of the probe in the improved detector according to FIG. 2, when the piston has been removed from the probe;

FIG. 4 is a bottom plan view of the piston in the improved detector and of a fragmentary portion of the protective casing, when both the sleeve and the housing have been removed from the probe;

DETAILED DESCRIPTION OF THE PREFERRED EMBODIMENT

Figure 1:
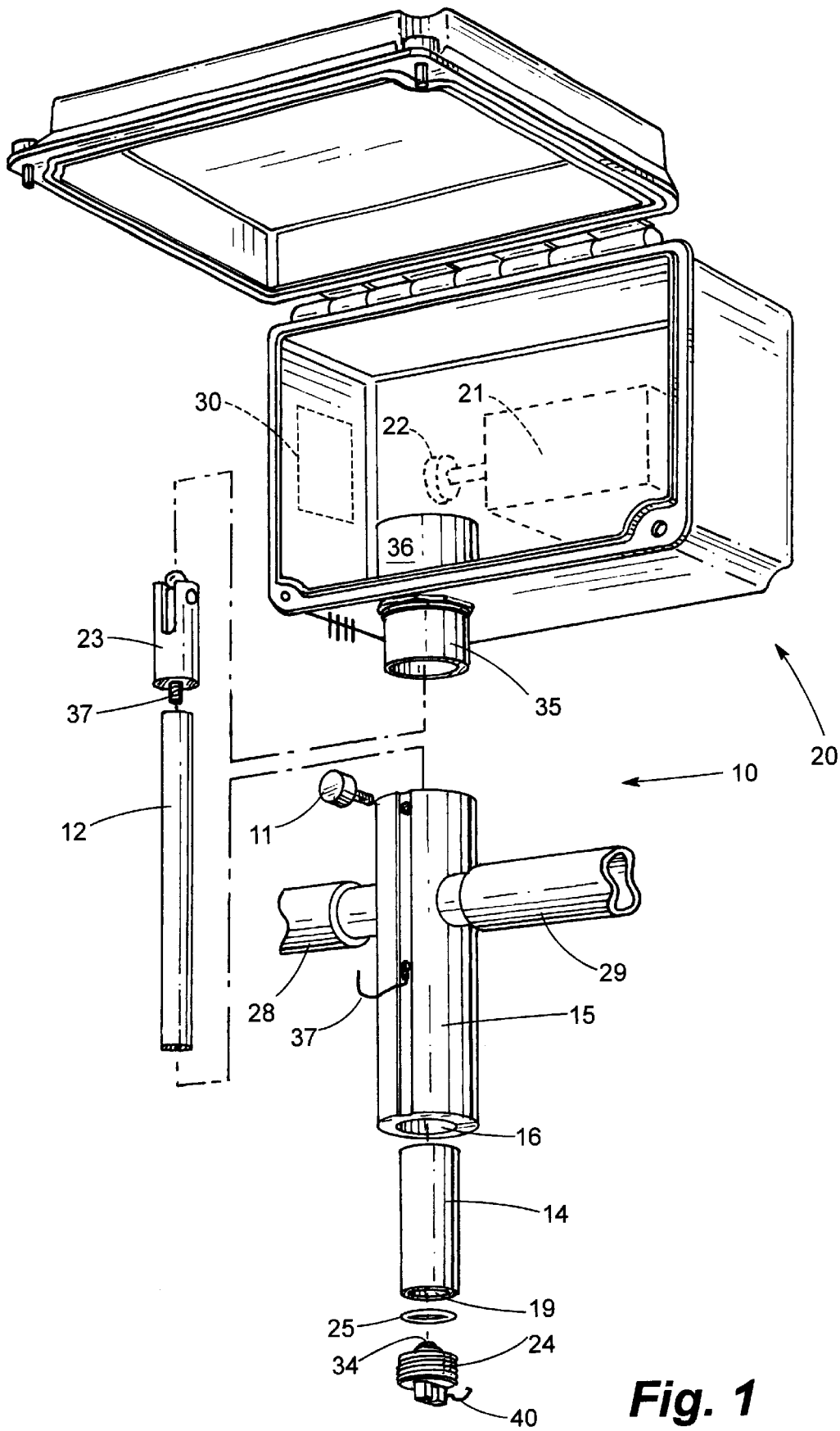
FIG. 1 is an exploded view of the improved streaming current detector with easily removable sleeve, piston, and electrodes, the detector including a protective casing shown with its door open, a driving gear for the piston and electronics circuit board being shown in dashed lines for illustrative purposes only and forming no part of the invention.
Figure 5:
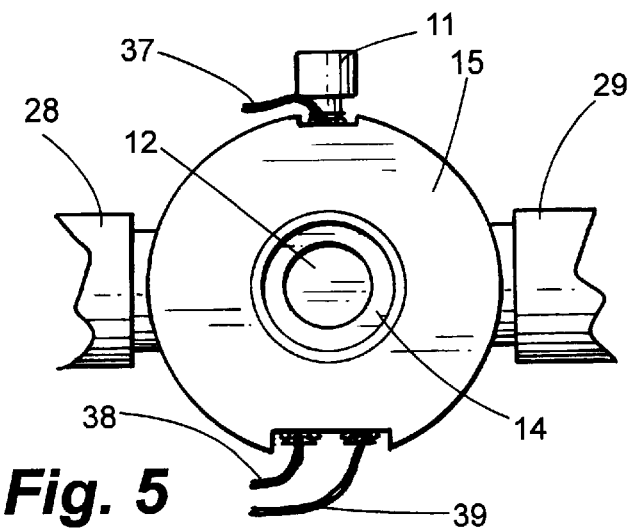
FIG. 5 is a bottom plan view of the probe in the improved detector, when the closure plug has been removed from the probe.

In the drawings, an improved streaming current detector, which is indicated generally by the reference numeral 10, comprises a probe with a housing 15 and an elongated hollow sleeve 14 for slideably receiving a reciprocating piston 12. Both the sleeve 14 and an active segment engageable therewith on the lower end of the piston 12 are fabricated of dielectric material, with the sleeve and the active segment having precision inner and outer surfaces, respectively. Clearances between these two surfaces measure, by way of example, about 0.005 inch.

Preferably, the sleeve 14 and the active segment are made of the same dielectric material, a material selected on the basis of its chemical and physical compatibility with the test fluid. Moreover, the clearance between these two dielectric elements is optimized for each specific application. Generally, narrower clearances produce a stronger signal because the streaming current is directly proportional to the velocity of the test fluid as it moves between the sleeve 14 and the active segment.

Figure 6:
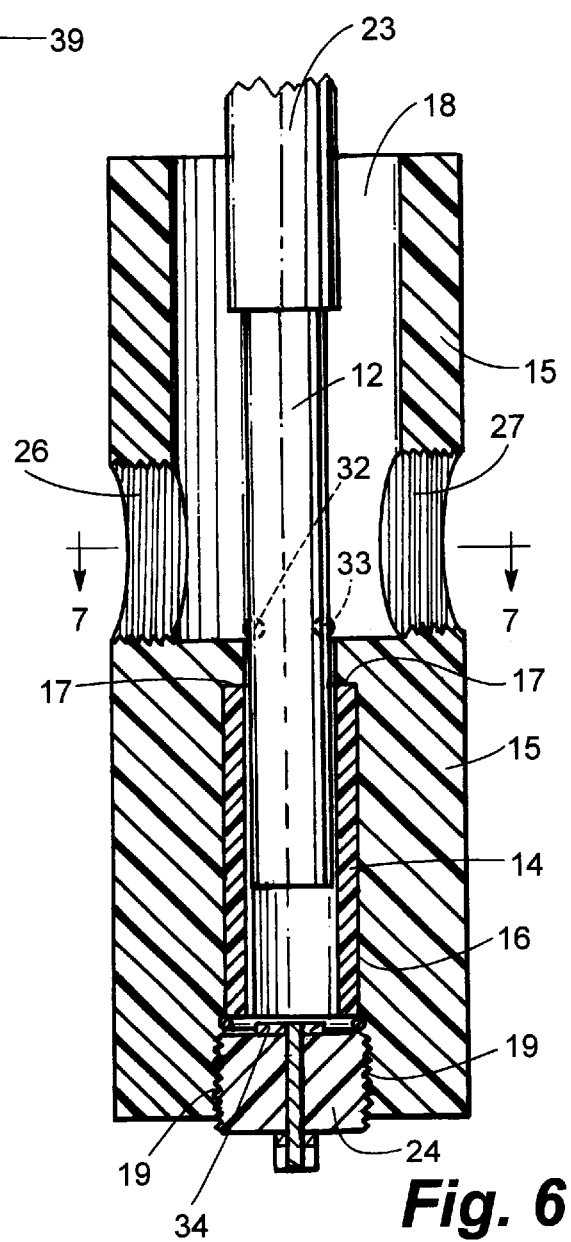
FIG. 6 is a cross section 6—6 through the probe in FIG. 3, but with the piston and a fragmentary portion of the guide included and both hoses disconnected from the inlet and outlet ports of the probe.

Prior to use, the sleeve 14 is slideably inserted into a cylindrical void 16 formed in the housing 15 and secured therewithin by a retaining fitting 24 (FIGS. 1 and 6). A shoulder 17 on the housing 15 forms a stop against which the upper end of the sleeve 14 abuts when it is inserted as far as possible into the housing. Engageable with internal threads 19, the retaining fitting 24, when tightened thereon, compresses a gasket 25 against the sleeve 14, forming a leak-tight seal between the fitting and the housing 15 (FIGS. 1 and 6).

As is best illustrated in FIG. 6, the housing also defines a transverse passageway fluidly connected to the sleeve 14. A test flow stream is directed through the transverse passageway via hoses 28, 29 secured to inlet and outlet ports 26, 27 (FIGS. 3 and 6). During upstrokes of the piston 12, samples of the flow stream are sucked into a narrow, elongated flow channel of capillary width formed between the active segment and the sleeve 14; and during downstrokes, the samples are expelled.

Figure 7:
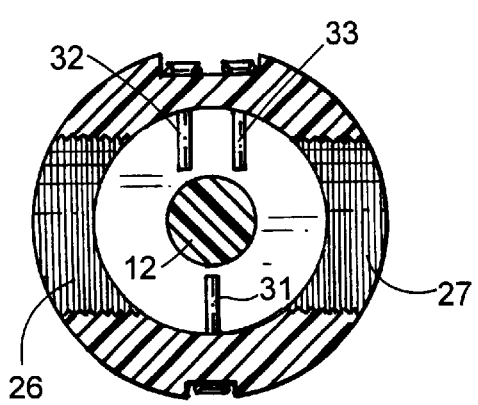
FIG. 7 is a cross-section 7—7 through the probe in FIG. 6.

Positioned proximate with the distal ends of the sleeve 14 is a first pair of sensing electrodes 31, 34, one of which is threadedly secured to the housing 15 and the other to the retaining fitting 24 (FIGS. 6 and 7). Spaced apart a distance greater than the longitudinal span of the sleeve 14, the electrodes 31, 34 are mounted so that they contact the sample flow stream just outside of the region where the close-fitting dielectric surfaces slide past each other (FIGS. 3, 6 and 7). Fluid, as it enters or leaves the narrow, elongated flow channel between them, still bathes both electrodes 31, 34. But, as is shown in FIGS. 3, 6 and 7, only a small tip of electrode 31 is disposed contiguous with the piston 12, reducing the likelihood of the electrode being broken and/or dislodged by grit or the like jamming between it and the piston 12. Similarly, in the case of electrode 34, which penetrates the retaining fitting 34 and protrudes slightly therefrom or, alternately, is recessed therewithin, the absence of shear forces acting upon the electrode as the piston 12 reciprocates, greatly reduces the chances of any catastrophic failure.

Moreover, each electrode 31, 34 can be threadedly advanced into the probe, so that the strength of the streaming current signal, diminished as electrode surfaces erode, can be restored. Conversely, the electrodes 31, 34 can be retracted independently of other probe elements when replacement is necessary. In the preferred embodiment, electrode 34 is mounted on a closure plug 24 and can also be discarded simply by unscrewing the latter.

Inspection and replacement of the piston 12, as well as of the housing 15 itself, is accomplished by first disengaging pinch bolt 11 (FIGS. 1 and 2). Affixed to the exterior wall of a protective casing 20 is a hollow support bushing 35 which, in the preferred embodiment, is threadedly joined, through an opening (not shown) in the casing to a hollow coupling 36. Complimenting the bushing 35 is a portion of the housing 15, distal from the sleeve 14, which defines an open cylindrical structure 18 (FIGS. 1, 4, 5 and 6). Prior to use, the structure 18 is slip fitted onto the bushing 35 and secured thereto by tightening the pinch bolt 11.

Moving through the support bushing 35, as the piston 12 reciprocates, is a guide 23 (FIGS. 4 and 6). The guide 23 defines an end which is releasably attached to the piston 12, preferably by threads 13 formed in the latter (FIG. 1). The guide 23 in turn has a yoke which is pinned to a crankshaft 22 (FIG. 1).

Acting through the guide 23 to force the piston 12 into repetitive upward and downward motions, the crankshaft 22 is driven by a synchronous motor 21 at a constant rpm (FIG. 1). This rotational speed is preferably 240 rpm. Means for generating a square wave signal as the crankshaft 22 is rotated is described in U.S. Pat. No. 4,769,608. A square wave signal is used to facilitate the detection of an alternating current generated when the active segment slides back and forth within the sleeve 14, repeatedly advancing and then retreating from the sensing electrode 34.

As an end of the active segment of the piston 12 moves closer to the electrode 34, an additional charge is induced thereon. An alternating current is generated at the frequency of the reciprocating piston 12. Means, including a filtering and synchronized measurement circuit, for processing this alternating signal, also known as the streaming current, so as to provide input to an indicating and control circuit 30 is disclosed in U.S. Pat. No. 4,769,608.

Figure 8:
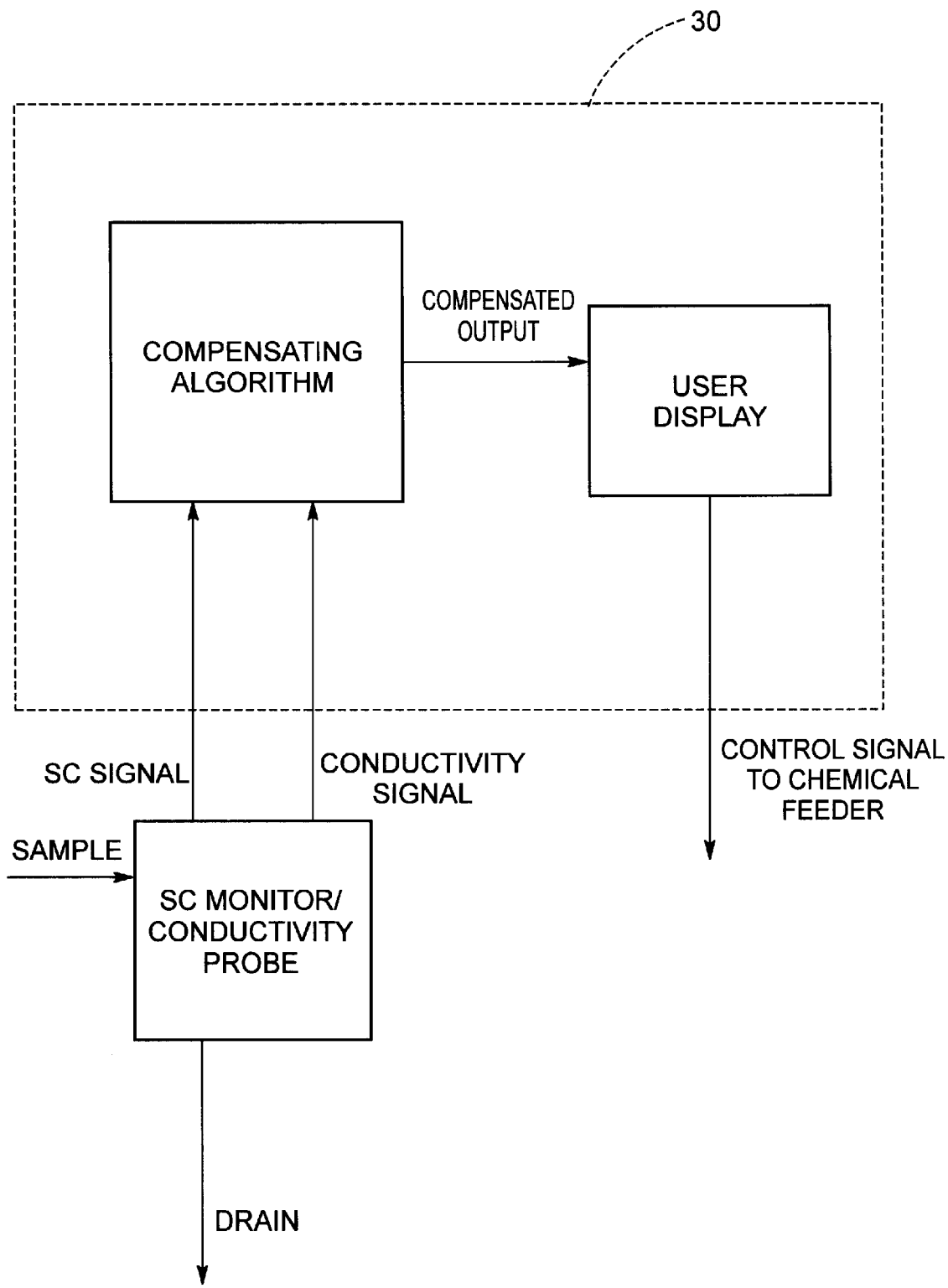
FIG. 8 shows a schematic of the signal processing equipment in which input from a conductivity probe is incorporated into the output from the improved streaming current detector.

As shown in the drawings, four electrical wires 37, 38, 39, 40 in the detector 10 connect electrodes to the circuit 30. In addition to the first pair of sensing electrodes 31, 34, a conductivity probe utilizing electrodes 32, 33 is preferably integrated into the detector 10. In the preferred embodiment, the electrodes 32, 33 are disposed generally in the same imaginary plane as is the electrode 31 (FIGS. 3, 6 and 7). This configuration enables all three electrodes 31, 32, 33 to be bathed simultaneously by the same sample of the test flow stream. A feed forward signal, proportional to a direct current flowing between the electrodes 32, 33 is used to increase or decrease the amplifier gain for the streaming current raw signal. The latter is modified in direct proportion to changes in the direct current using the following compensating algorithm:

$$SC=(ZP-B)/mC,$$

where SC is the streaming current; ZP, the zeta potential; C, the conductance of the test fluid; and m and B, the slope and offset, respectively. A schematic of signal processing equipment in which input from the conductivity probe is incorporated into output from the electrodes 31, 34 is shown in FIG. 8. Alternately, the conductivity of the test fluid can be measured and displayed independently of the steaming current.

Each of the sensing electrodes 32, 33 is threadedly engaged with the housing 15 and, like the sleeve 14, the reciprocating piston 12, and the electrodes 31, 34, can be removed independently of other probe elements. Generally, removal and replacement of each probe element that comes into contact with the test fluid can be accomplished in the field in under one minute.

It is understood that those skilled in the art may concive other applications, modifications and/or changes in the invention described above. Any such applications, modifications or changes which fall within the purview of the description are intended to be illustrative and not intended to be limitative. The scope of the invention is limited only by the scope of the claims appended hereto.

Having described the invention, what is claimed is:

1. An apparatus for measuring the streaming current in a sample flow stream of a fluid containing charged species, comprising:
   a. a housing having a transverse passageway through which the stream can flow, the housing defining a cylindrical void disposed perpendicularly to the transverse passageway and to one side thereof;
   b. an elongated, hollow sleeve made of an electrically insulating material, the sleeve being disposed within the cylindrical void and slideably removable therefrom, the sleeve being fluidly connected to the transverse passageway;
   c. means for retaining the sleeve in a fixed position relative to the housing;
   d. a reciprocating element whose outer wall is electrically insulating and which is disposed in slideable relationship with said sleeve, the reciprocating element having an active segment, the active segment having a transverse cross-section such that the segment slip fits within the sleeve, the active segment and the sleeve together forming at least one narrow, elongated flow channel of capillary width between the active segment and the sleeve;
   e. a pair of sensing electrodes which are mounted within the housing, a first sensing electrode being disposed near the sleeve retaining means and a second sensing electrode nearer the transverse passageway, each electrode being situated proximate with one of the distal ends of the sleeve, said pair of electrodes being spaced apart a distance greater than the longitudinal span of the sleeve, both electrodes being so disposed as to be contacted by the fluid entering or leaving said flow channel, the sleeve being slideably removable from the cylindrical void independently of any removal of the second electrode from the housing;
   f. means for moving the reciprocating element in said sleeve so that the element reciprocates at a constant frequency; and
   g. means coupled to said electrodes for detecting an alternating current flowing between said electrodes that is generated at the frequency of the reciprocating element.

2. The apparatus according to claim 1 which further comprises means for threadedly advancing the first electrode in a direction parallel to the longitudinal centerline of the sleeve, so that as exposed surfaces of the first electrode erode, the amplitude of said alternating current can be substantially restored.

3. The apparatus according to claim 1 wherein the means for moving the reciprocating element further comprises a guide, a portion of the reciprocating element distal from the active segment being releasably attached to the guide, so that both the sleeve and the reciprocating element can be easily replaced at the same time, allowing the sleeve and the active segment to be selected, as a set, on the basis of their chemical and physical compatibility with the sample flow stream.

4. The apparatus according to claim 1 wherein the means for moving the reciprocating element further comprises a guide, a portion of the reciprocating element distal from the active segment: being releasably attached to the guide, so that both the sleeve and the reciprocating element can be easily replaced at the same time, allowing the sleeve and the active segment to be selected, as a set, on the basis of the width, in transverse cross-section, of the flow channel which the sleeve and active segment together form, thereby mechanically adjusting the strength of the alternating current flowing between the sensing electrodes.

5. The apparatus according to claim 1 wherein the sleeve retaining means comprises a closure cap which, in use, is threadedly engaged with the housing, the first sensing electrode being mounted on the closure cap and removable therewith.

6. An apparatus for measuring the streaming current in a sample flow stream of a fluid containing charged species, comprising:

a. a housing having a transverse passageway through which the stream can flow, the housing defining a cylindrical void disposed perpendicularly to the transverse passageway and to one side thereof;

b. an elongated, hollow sleeve made of an electrically insulating material, the sleeve being disposed within the cylindrical void and slideably removable therefrom, the sleeve being fluidly connected to the transverse passageway, the sleeve consisting of a simple cylindrical structure resembling a pipe segment;

c. means for retaining the sleeve in a fixed position relative to the housing;

d. a reciprocating element whose outer wall is electrically insulating and which is disposed in slideable relationship with said sleeve, the reciprocating element having an active segment, the active segment having a transverse cross-section such that the segment fits snugly within the sleeve, the active segment and the sleeve together forming at least one narrow, elongated flow channel between the active segment and the sleeve;

e. a pair of sensing electrodes which are mounted within the housing, a first sensing electrode being disposed near the sleeve retaining means, each electrode being situated proximate with one of the distal ends of the sleeve, said pair of sensing electrodes being spaced apart a distance greater than the longitudinal span of the sleeve, both electrodes being so disposed as to be contacted by fluid entering or leaving said flow channel;

f. means for moving both the active segment of the reciprocating element in the sleeve and a portion of the sample flow stream in and out of the sleeve, the element reciprocating at a constant frequency; and g. means coupled to the sensing electrodes for detecting an alternating current flowing between the sensing electrodes that is generated at the frequency of the reciprocating element.

7. In an apparatus for determining a function of the electric charge condition in a sample flow stream of a fluid containing electrical charge influencing species, said apparatus comprising:

a. a housing having a transverse passageway through which the stream can flow;

b. an elongated, hollow sleeve made of an electrically insulating material, the sleeve being disposed within the housing and slideably removable therefrom, the sleeve being fluidly connected to the transverse passageway;

c. means for retaining the sleeve in a fixed position relative to the housing;

d. a reciprocating element whose outer wall is electrically insulating and which is disposed in slideable relationship with said sleeve, the reciprocating element having an active segment, the active segment having a transverse cross-section such that the segment fits snugly within the sleeve, the active segment and the sleeve together forming at least one narrow, elongated flow channel between the active segment and the sleeve;

e. a set of four sensing electrodes which are mounted within the housing, a first sensing electrode being disposed near the sleeve retaining means and second, third and fourth sensing electrodes nearer the transverse passageway, each electrode being situated proximate with one of the distal ends of the sleeve, the first and second sensing electrodes being spaced apart a distance greater that the longitudinal span of the sleeve, all four electrodes being so disposed as to be contacted by fluid entering or leaving said flow channel;

f. means for moving the reciprocating element in said sleeve so that the element reciprocates at a constant frequency;

g. means coupled to said first and second sensing electrodes for detecting an alternating current flowing therebetween that is generated at the frequency of the reciprocating element; and h. means coupled to said third and fourth sensing electrodes for detecting a direct current flowing therebetween, the magnitude of said alternating current being modified in direct proportion to changes in said direct current, so that a conductivity compensated output is generated.

8. An apparatus for measuring the streaming current in a sample flow stream of a fluid containing charged species, comprising:

a. a housing having a transverse passageway through which the stream can flow, the housing defining a cylindrical void disposed perpendicularly to the transverse passageway and to one side thereof;

b. an elongated, hollow sleeve made of an electrically insulating material, the sleeve being disposed within the cylindrical void and slideably removable therefrom, the sleeve being fluidly connected to the transverse passageway;

c. means for retaining the sleeve in a fixed position relative to the housing;

d. a reciprocating element whose outer wall is electrically insulating and which is disposed in slideable relationship with said sleeve, the reciprocating element having an active segment, the active segment having a transverse cross-section such that the segment slip fits within the sleeve, the active segment and the sleeve together forming at least one narrow, elongated flow channel of capillary width between the active segment and the sleeve;

e. a pair of sensing electrodes with are mounted within the housing, a first sensing electrode being disposed near the sleeve retaining means and a second sensing electrode nearer the transverse passageway, each electrode being situated proximate with one of the distal ends of the sleeve, said pair of electrodes being spaced apart a distance greater than the longitudinal span of the sleeve, both electrodes being so disposed as to be contacted by the fluid entering or leaving said flow channel, the second electrode including a tip which is disposed in close proximity to the reciprocating element and which is situated within the transverse passageway;

f. means for moving the reciprocating element in said sleeve so that the element reciprocates at a constant frequency; and g. means coupled to said electrodes for detecting an alternating current flowing between said electrodes that is generated at the frequency of the reciprocating element.

* * * * *